United States Patent [19]
Starkweather et al.

[11] Patent Number: 5,792,188
[45] Date of Patent: Aug. 11, 1998

[54] CAPACITOR REFORMATION AND MEASUREMENT IN AN IMPLANTABLE CARDIOVERTER/DEFIBRILLATOR (ICD)

[75] Inventors: Timothy J. Starkweather, Boulder Creek; Kelly H. McClure, Simi Valley; Min-Yaug Yang, Monterey Park, all of Calif.

[73] Assignee: Pacesetter, Inc., Sylmar, Calif.

[21] Appl. No.: 789,324

[22] Filed: Jan. 23, 1997

[51] Int. Cl.$^6$ ............................................. A61N 1/08
[52] U.S. Cl. ................................................. 607/5
[58] Field of Search ................................. 607/5, 6, 7, 8

[56] References Cited

U.S. PATENT DOCUMENTS

| | | |
|---|---|---|
| 4,295,474 | 10/1981 | Fischell . |
| 4,300,567 | 11/1981 | Kolenik et al. . |
| 4,384,585 | 5/1983 | Zipes . |
| 4,693,253 | 9/1987 | Adams . |
| 4,712,555 | 12/1987 | Thornander et al. . |
| 4,787,389 | 11/1988 | Tarjan . |
| 4,809,697 | 3/1989 | Causey et al. . |
| 4,940,052 | 7/1990 | Mann et al. . |
| 4,944,299 | 7/1990 | Silvian . |
| 4,989,602 | 2/1991 | Sholder et al. . |
| 5,318,591 | 6/1994 | Causey et al. ........................ 607/5 |
| 5,350,402 | 9/1994 | Infinger et al. ........................ 607/5 |
| 5,350,405 | 9/1994 | Silvian ................................... 607/7 |
| 5,425,749 | 6/1995 | Adams .................................. 607/5 |
| 5,470,342 | 11/1995 | Mann et al. ........................... 607/5 |

*Primary Examiner*—Scott M. Getzow

[57] ABSTRACT

An implantable cardioverter defibrillator (ICD) device provides capacitor reformation by successively charging and leaking its output capacitor either a specified number of times or until a specified charge remains on the output capacitor after leakage. The ICD delivers therapy with minimal delay should an arrhythmia detection occur during the capacitor reformation process by anticipating an arrhythmia detection and dumping the reformation energy stored on the output capacitor to an acceptable level as soon as a possible arrhythmia detection is anticipated. The ICD further measures the energy level of the last charge delivered following each delivery so that the energy level of subsequent charges may be adjusted to provide optimal therapy to the patient if prior therapy attempts have not successfully terminated the arrhythmia.

34 Claims, 6 Drawing Sheets

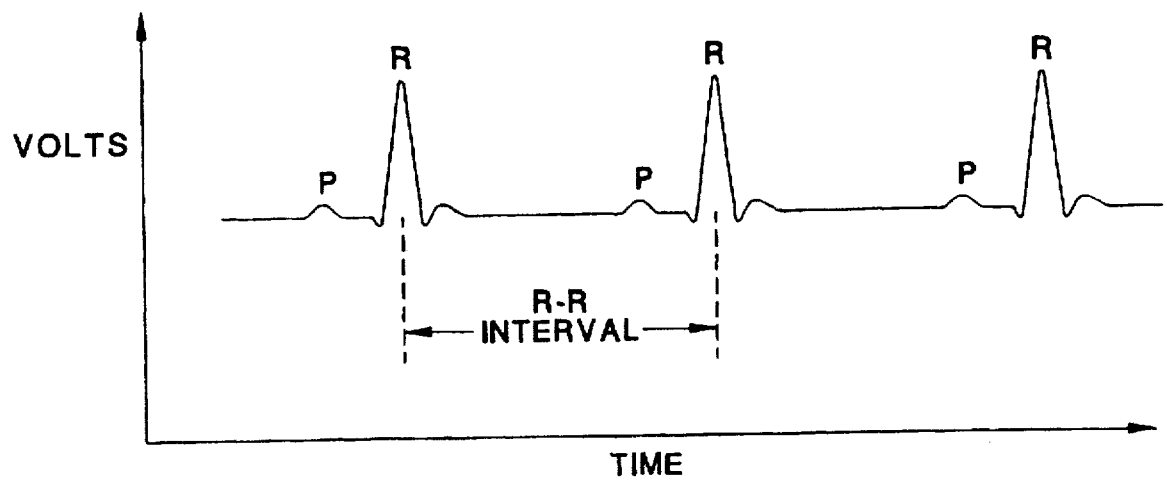
FIG. 2
| RATE ZONE | LOWER LIMIT | UPPER LIMIT |
|-----------|-------------|-------------|
| VF | ≥ 240 bpm | |
| VT2 | ≥ 200 bpm | < 240 bpm |
| VT1 | ≥ 150 bpm | < 200 bpm |
FIG. 3
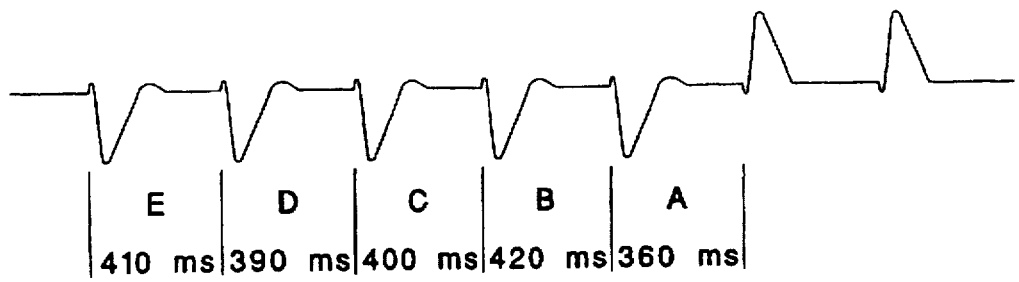
FIG. 4A

CAPACITOR REFORMATION AND MEASUREMENT IN AN IMPLANTABLE CARDIOVERTER/DEFIBRILLATOR (ICD)

FIELD OF THE INVENTION

The present invention relates to implantable medical devices and methods, and more particularly to an implantable cardioverter/defibrillator (ICD) device which: provides optimal capacitor reformation by successively charging and leaking its output capacitor a specified number of times; delivers a shock therapy with minimal delay once an arrhythmia detection occurs during the capacitor reformation process; and measures the energy level of the last charge delivered following each delivery so that the energy level of subsequent charges, if needed, may be adjusted to provide optimal therapy.

BACKGROUND OF THE INVENTION

It is the primary function of an implantable cardioverter-defibrillator (ICD) device to sense the occurrence of an arrhythmia, and to automatically apply an appropriate shock therapy to the heart aimed at terminating the arrhythmia. Although there are many shock therapy protocols which an ICD may follow in its attempt to terminate an arrhythmia, most modern ICD devices provide tiered level therapies, each level of therapy corresponding to different types of arrhythmias and providing a specified number of shocks of varying energies and pulse durations in order to most efficiently terminate the specific type of arrhythmia detected.

Typically, an arrhythmia is a rapid irregular rhythm of the heart, e.g., ventricular tachycardia or ventricular fibrillation. For purposes of the present invention an arrhythmia may also include atrial tachycardia, atrial fibrillation, as well as asystole (a stopped heart). As used hereinafter, the term "arrhythmia" is used broadly to indicate any irregular rhythm of the heart that interferes with the heart's ability to perform its basic function of a pump.

It is known in the ICD art to provide a tiered therapy with regard to the termination of sensed arrhythmias. The term "tiered" therapy has been used typically to describe the different arrhythmia rate zones, such as low rate ventricular tachycardia (VT Low), high rate tachycardia (VT High), and ventricular fibrillation (VF). The term "tiered therapy" also has been used to describe the increasing degree of aggressiveness of therapy within each rate zone. For example, within each zone the physician may program the number of stimulation pulses, the interval between stimulation pulses, the energy level of the stimulation, and the number of attempts, etc. Thus, based upon the detected rate of the arrhythmia, the ICD will continue to increase the level of aggressiveness until such arrhythmia is terminated.

In all tiered therapy ICD devices, each tier of therapy is programmed to provide one or more shocks of specified energy values. Typically, each successive shock within a given tier is of greater energy than a prior shock within that tier and the shock energies corresponding to a given tier of therapy are greater for higher rate zones, i.e., ventricular fibrillation, than lower rate zones, i.e., low rate tachycardia.

In order to apply an electrical shock to the heart (whether of low, moderate, or high energy), it is first necessary to charge an output capacitor of the ICD device with an electrical charge of the desired energy. Appropriate electrodes are then coupled to the capacitor through an appropriate output switch. When an electrical stimulation pulse is to be applied to the heart, the appropriate output switch is closed to connect the output capacitor to the cardiac tissue through the electrodes, thereby effectively "dumping" the charge stored in the output capacitor into the cardiac tissue.

There are many types of electrodes which can deliver the energy shock on the output capacitor to the heart. The electrode system can be epicardial (attached to the external surface of the heart) or endocardial (attached to the internal surface of the heart) or patch (attached to the skin proximate to the heart), or any combination of epicardial, endocardial or patch electrodes. Such electrodes are well known in the art. See, e.g., U.S. Pat. No. 4,662,377 (Heilman et al.), issued May 5, 1987, entitled "Cardioverting Method and Apparatus Utilizing Catheters and Patch Electrodes"; U.S. Pat. No. 4,481,953 (Gold et al.), issued Nov. 13, 1984, entitled "Endocardial Lead Having Helically Wound Ribbon Electrode"; and U.S. Pat. No. 4,010,758 (Rockland et al.), issued Mar. 3, 1977, entitled "Bipolar Body Tissue Electrode," which patents are hereby incorporated herein by reference. Hereinafter, the electrodes (whether patch, epicardial, or endocardial, etc.) will be referred to as simply "electrodes."

The use of electrolytic capacitors for the storage of energy necessary for high voltage shocks during implantable cardioverter defibrillation (ICD) therapy is currently universal. However, use of these electrolytic capacitors for a device with an estimated lifetime of several years necessitates periodic reformation to maintain the physical characteristics of the capacitors. This reformation is typically achieved by charging the capacitors to their maximum rated energy levels and then allowing the charge to gradually leak for a specified period of time. Variations of this technique exist, but this is the general process for capacitor reformation which is based on the chemical composition of electrolytic capacitors and the chemical reactions thereof, which are well known in the art.

In prior art ICD's, during the capacitor reformation process when the capacitor is charged to a high voltage and allowed to leak for a specified period of time, a window of time exists where this process can interfere with the programmed shock energies for an arrhythmia therapy. Upon detection of an arrhythmia, all prior art ICD's, of which Applicants are aware, simply deliver the energy on the capacitor during the reformation period or the programmed energy, whichever is greater. Because the charge energy stored on the capacitor during capacitor reformation is at or near the maximum energy level capable of being stored on the capacitor, delivery of this charge to a patient may overdose the patient with charge energy. Typical charge energies during capacitor reformation are approximately 30–40 joules. Therefore, a patient undergoing an arrhythmia which requires only 1 to 10 joules to terminate the arrhythmia will be unnecessarily and detrimentally overdosed with charge energy if he or she is exposed to the 30–40 joules stored on the capacitor during capacitor reformation. One solution to this charge overdose problem is to dump the charge on the capacitors to the programmed level in the event that an arrhythmia detection occurs. However, this technique results in a delay of therapy which may also be detrimental to the patient.

It is well known in the ICD art that the chance of terminating an arrhythmia in a patient is inversely proportional to the length of time it takes for therapy to be delivered to the patient. Therefore, all ICD devices currently on the market, of which Applicants are aware, avoid any unnecessary delays of therapy to the patient and deliver the full charge on the capacitor at the time of arrhythmia detection. However, because this prior art implementation leads to the possibility that the shock energy delivered is greater than the shock energy programmed by the physician, this prior art ICD implementation creates the possibility of overdosing the patient with charge energy. In addition, prior art ICD's do not take any measures to determine the appropriateness of subsequent therapy.

To further illustrate the problems associated with charge overdosing, consider the following example: a particular rate zone is programmed with first shock at 2 joules, a second shock at 5 joules, and a third shock at 10 joules. Capacitor reformation is in progress when an arrhythmia event is detected within the rate zone. In response to detecting the arrhythmia event, the ICD delivers the full charge on the capacitor at the time of detection. Thus, a 30 to 40 joule shock could be delivered as the first shock; which, if failing to convert the patient (terminate the arrhythmia), would then be followed by the second shock, which is only a 5 joule shock.

When shock therapy is successively applied during an arrhythmia episode, a general rule that should be followed by all tiered therapy ICD devices is that the shock energy be increased from one redetection to the next, never decreased. The only exception to this rule is if the shock energy is already at a maximum level available from the ICD. As described in the example above, prior art ICD's do not always follow this general rule if a shock is delivered while capacitor reformation is in process. Rather, as the above example shows, the first shock could be of greater energy than the programmed first shock, which means that a subsequent shock may not always be of greater energy than a prior shock, resulting in the delivery of suboptimal therapy to the patient.

Because of the above-described problems associated with capacitor reformation, prior art ICD's typically try to minimize the window of time, i.e., the capacitor reformation period, during which these problems could occur. Therefore, prior art capacitor reformation processes consist of a one-time charging of the capacitor to its maximum voltage and allowing this charge to leak for a specified (short) period of time. Unfortunately, charging and quickly discharging a capacitor a single time in this manner is both inefficient and does not allow an accurate measure of the capacitance to be made.

An accurate measure of the capacitance of the output capacitor is extremely important in an ICD device in order to calibrate the high voltage values on the capacitor so that the actual amount of stored energy can be correctly calculated. An accurate measure of the capacitance is best made by charging and discharging the capacitor a number of times in rapid succession. Such successive charging/discharging also increases the longevity of the capacitor. Thus, prior art ICD's which minimize the window of time in which a charge is placed on a capacitor and allowed to discharge therefrom by using a relatively quick one-time charge and discharge not only provide suboptimal capacitor reformation, but also lead to inaccurate capacitance measurement.

Thus, it is apparent that an ICD device is needed that implements a capacitor reformation protocol that allows optimal reformation of the capacitor and accurate capacitance measurement by successive charging and leaking of the capacitor until leakage is minimized, while avoiding any unnecessary delays of treatment which may be detrimental to the patient in the event an arrhythmia event is detected during the optimal capacitor reformation process. In addition, it is evident that what is further needed is an ICD device that avoids overdosing the patient with charge energy in the event a charge is delivered during the capacitor reformation process, and which provides appropriate subsequent therapy in the event the first-delivered therapy is not successful.

SUMMARY OF THE INVENTION

The present invention addresses the above and other needs by providing an implantable cardioverter-defibrillator (ICD) that provides optimal capacitor reformation, i.e., successive charging and leaking the output capacitor a specified number of times, or until leakage does not exceed a minimum leakage threshold value, while avoiding any unnecessary delays of therapy to the patient in the event an arrhythmia event is detected during the capacitor reformation process. The ICD accomplishes these goals by beginning to dump the charge on the output capacitor to a programmed level as soon as an arrhythmia event is anticipated, prior to actually detecting an arrhythmia event. Thus, by the time the actual arrhythmia event is detected, the charge on the output capacitor has been sufficiently reduced to prevent serious overdosing of the patient. When the actual arrhythmia event is detected, dumping of the output capacitor ceases and the remaining charge on the capacitor is delivered to the patient regardless of whether the charge on the capacitor has reached the programmed energy level. In this way, delay is minimized from the point of arrhythmia detection to the point of therapy delivery.

Following each delivery of charge to the patient, the ICD measures the shock energy delivered and sets subsequent shock energies to appropriate levels (i.e., of increasing value) so that optimal therapy may be delivered to the patient if arrhythmia events are subsequently redetected. Therefore, the ICD of the present invention ensures that each successive shock delivered to a patient during a single arrhythmia episode is of greater shock energy than the previously delivered shock, unless the maximum shock energy level has already been delivered, in which case, the maximum shock energy is redelivered upon a subsequent arrhythmia event redetection.

In accordance with one aspect of the invention, an implantable cardioverter-defibrillator (ICD) device is provided that includes: an output capacitor; means for placing a programmed energy level on the output capacitor; means for reforming the output capacitor; means for anticipating an arrhythmia event during capacitor reformation; means for dumping the energy level on the output capacitor to the programmed energy level if an arrhythmia event is anticipated while reforming the capacitor; means for ceasing the dumping of the output capacitor in the event an arrhythmia event is actually detected; and means for delivering the charge on the output capacitor to the patient immediately after the detection of an arrhythmia event.

In accordance with an additional aspect of the invention, a method is provided of reforming an output capacitor of an implantable cardioverter-defibrillator (ICD). Such method includes the steps of: (a) reforming the output capacitor by charging the output capacitor to its maximum charge value and allowing the charge to leak off for a specified period of time; (b) checking for a possible arrhythmia event while the output capacitor is being reformed in accordance with step (a); (c) dumping the charge on the output capacitor to a programmed energy level if a possible arrhythmia event is anticipated; and (d) determining whether an arrhythmia event is detected, and if so ceasing the dumping of the output capacitor and delivering to the patient whatever charge is on the output capacitor at the time the arrhythmia event is detected.

The present invention contemplates that the reformation of the output capacitor (step (a) above) may be achieved in several ways. One way of reforming the output capacitor comprises charging the output capacitor to its maximum energy level and allowing the charge to leak off for a specified time period, and then repeating this charging-and-leaking-for-a-specified-time-period process a specified number of times. The number of recharges, for example, may be specified by a recharge parameter, and the interval between successive recharges may be specified by a leak-time parameter, and these parameters may be programmed into a memory of the ICD.

Another way of reforming the output capacitor includes charging the output capacitor to its maximum energy level and allowing the charge to leak off for a specified time period and then checking to see if the charge remaining on the capacitor, after the specified time period, exceeds a specified charge level. If not, this process of charging-and-leaking-and-checking-for-a-specified-charge-level after the specified time period is repeated until the voltage remaining on the capacitor after the specified time period exceeds the specified charge level (which if it does indicates the capacitor has been sufficiently reformed to reduce its leakage to the point that the charge remains above the specified charge level after the specified time period). When the charge remains above the specified threshold after the specified time, this ensures that the reformation process has continued for an adequate number of "reforming" cycles. The threshold level to which the charge is to leak may be specified by a programmable leakage threshold parameter.

In accordance with a further aspect of the invention, the implantable cardioverter-defibrillator (ICD) provides a tiered shock therapy which causes successive shocks delivered to a patient to always be of increasing magnitude, even if the need for such shock therapy arises during a capacitor reformation process. The ICD includes means for sensing an arrhythmia event through one or more electrodes adapted to be coupled to a patient's heart. The ICD further includes an output capacitor that is electrically connected to the one or more electrodes through an output switch. A charging circuit in the ICD charges the output capacitor to a specified energy level. A control circuit within the ICD, e.g., a microprocessor-based controller, generates control signals which control the charging circuit and output switch in accordance with a prescribed tiered therapy protocol. The control circuit includes a memory wherein programmed parameter values are stored which define charge energy values for each level of the tiered therapy. The control circuit includes means for measuring the energy delivered by the output capacitor following each charge delivery, and means for comparing the measured energy to a programmed parameter value stored in the memory. If the measured energy is greater than the programmed parameter value for the appropriate tier of the tiered therapy, then a search of the parameter values stored in the memory is undertaken to find the next programmed parameter value that is greater than the measured energy. The value of a next shock energy to be delivered to the patient is then set to this next programmed parameter value. Thus, in this way, subsequent shocks delivered as part of the tiered therapy, if needed, are always of increasing magnitude.

In accordance with yet another aspect of the invention, a method is provided for dynamically adjusting the charge energy values delivered to a patient by an implantable cardioverter defibrillator (ICD) device. More particularly, the method involves adjusting the delivered charge energy values to appropriate programmed energy levels following every charge delivery to a patient. The method involves first measuring the charge delivered by the ICD following each charge delivery, and then comparing the delivered charge thus measured to a programmed parameter corresponding to a desired charge energy value for the selected therapy. In the event that the measured energy is found to be greater than the desired programmed parameter, then the method further involves automatically adjusting the ICD so that the next charge energy value delivered to the patient, if needed, will be greater than the measured energy, thereby assuring that the patient receives charge energy values of increasing magnitude.

It is thus a feature of the present invention to provide an implantable cardioverter-defibrillator (ICD) device that provides successive charges and discharges of the output capacitor, thereby achieving optimal capacitor reformation, yet prevents overdosing and unnecessary delays in the delivery of needed shock therapy to a patient should an arrhythmia event occur during the capacitor reformation process. Overdosing and delays are avoided by anticipating the occurrence of an arrhythmia event (as opposed to waiting until an actual arrhythmia event occurs) and by beginning to discharge the output capacitor as soon as the arrhythmia event is anticipated. Thus, by the time the actual arrhythmia event is detected, the charge on the output capacitor has been sufficiently reduced to prevent serious overdosing of the patient, and such charge can be immediately delivered to the patient, without delay.

It is another feature of the invention to provide such an ICD device (which begins early discharging of the output capacitor upon anticipation of an arrhythmia event) wherein the charge remaining on the output capacitor at the time an arrhythmia event is actually detected is immediately delivered to the patient, regardless of whether this charge has reached its programmed energy level.

It is yet an additional feature of the invention to provide a tiered-therapy ICD device wherein the output charge actually delivered to a patient is measured so that any subsequent shocks that have to be delivered to the patient as part of the same tiered therapy can be adjusted, as required, to ensure they are of increasing magnitude.

BRIEF DESCRIPTION OF THE DRAWINGS

The above and other aspects, features and advantages of the present invention will be more apparent from the following more particular description thereof, presented in conjunction with the following drawings, wherein:

FIG. 2 shows an electrogram (EGM) waveform which depicts the cardiac activity of a patient, and which illustrates how the ventricular intervals (R-to-R intervals) may be used to monitor the heart rate of the patient in order to anticipate and detect cardiac arrhythmias;

FIG. 3 is a table that defines arrhythmia rate-zone classifications in accordance with a typical ICD tiered therapy;

FIGS. 4A and 4B schematically show EGM waveforms and illustrate how the present invention defines and uses a Sudden Onset Criteria to help anticipate the occurrence of an arrhythmia event;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
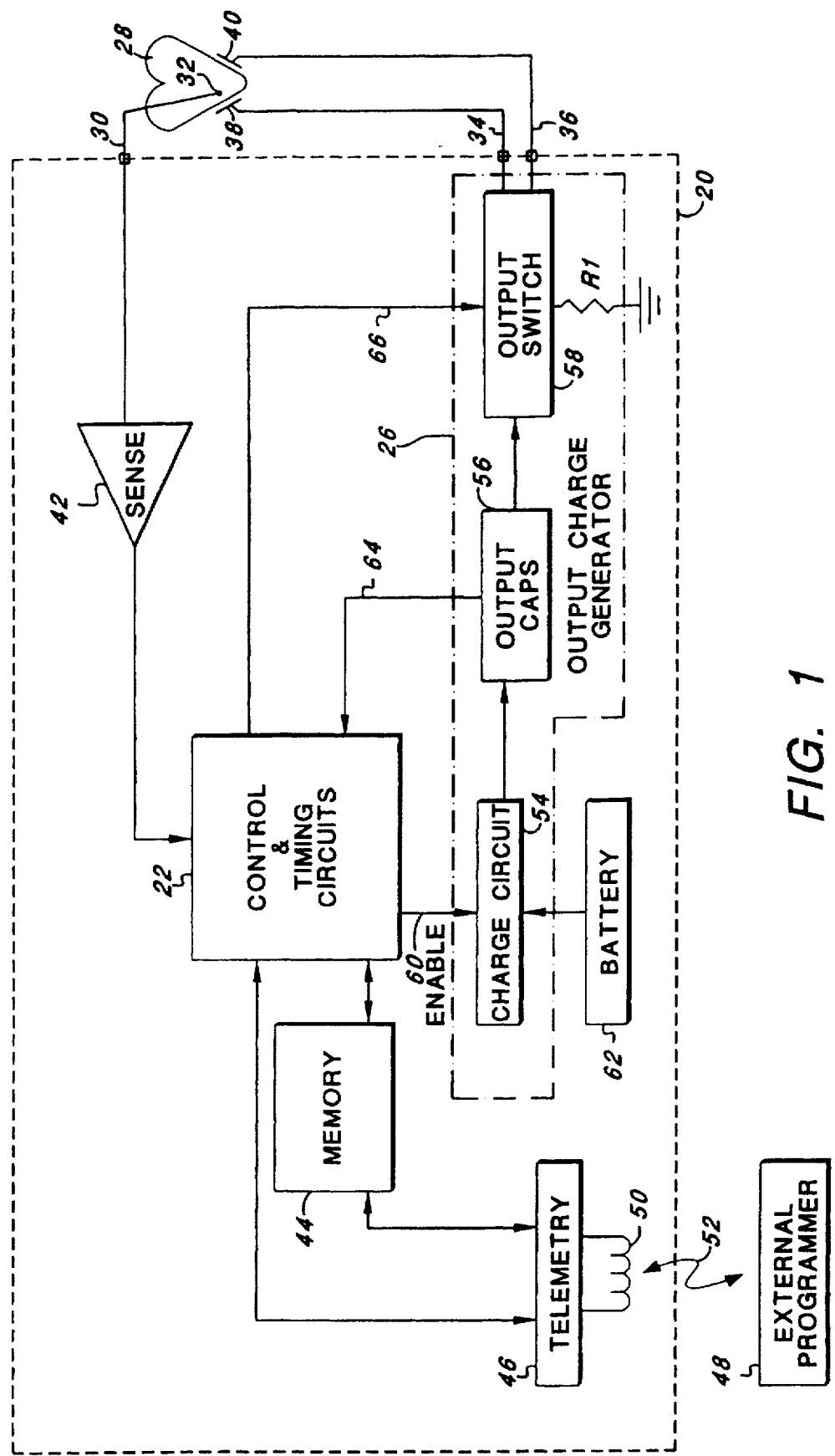
FIG. 1 shows a simplified functional block diagram of an implantable cardioverter-defibrillator (ICD) capable of providing capacitor reformation and shock therapy in accordance with the present invention.

To better understand the present invention, it will first be helpful to have a basic understanding of an implantable cardioverter-defibrillator (ICD) device, and the manner in which such an ICD device is typically programmed to operate. It is the primary function of an ICD device to sense the occurrence of an arrhythmia, and to automatically apply an appropriate electrical shock therapy to the heart aimed at terminating the arrhythmia. To this end, an ICD device 20, as shown in the functional block diagram of FIG. 1, includes control and timing circuits 22 (hereafter "control/timing" circuit 22) that control an output charge generator 26. The output charge generator 26 generates output electrical stimulation pulses of moderate or high energy (cardioversion or defibrillation pulses), e.g., electrical pulses having energies of from 1 to 10 joules (moderate) or 11 to 40 joules (high), as controlled by the control/timing circuit 22. Such moderate or high energy pulses are applied to the patient's heart through at least two leads 34 and 36, each of which is respectively coupled to a suitable implanted electrode 38 or 40 positioned to be in contact with the heart 28. Typically, the electrodes 38 and 40 are patch electrodes that are placed in contact with, or near, external cardiac tissue. The electrodes 38 and 40 may be of conventional design, and may be implanted using known techniques, as shown, e.g., in U.S. Pat. Nos. 4,774,952 (Smits); 4,991,603 (Cohen et al.) and 4,998,975 (Cohen et al.), incorporated herein by reference. While only two leads and electrodes are shown in FIG. 1, it is to be understood that additional defibrillation leads and electrodes may be used as desired or needed in order to efficiently and effectively apply the shock treatment generated by the high voltage generator 26 to the patient's heart 28.

The ICD 20 also includes a sense amplifier 42 that is coupled to sensing lead 30 and electrode 32. It is the function of the sense amplifier 42 to sense the activity of the heart 28 as manifest by the presence of certain electrical signals sensed through the electrode 32. That is, as is known in the art, R-waves occur upon the depolarization, and hence contraction, of ventricular tissue; and P-waves occur upon the depolarization, and hence contraction, of atrial tissue.

Thus by sensing R-waves and/or P-waves through the sense amplifier 42, and providing such sensed signals to the control/timing circuit 22, the control/timing circuit 22 is able to make a determination as to the rate and regularity of the patient's heart beat. Such information, in turn, allows the control/timing circuit 22 to determine whether the heart 28 of a patient is experiencing an arrhythmia.

The control/timing circuit 22 further has a memory circuit 44 coupled thereto wherein the operating parameters used by the control/timing circuit 22 are stored. Such operating parameters define, for example, the amplitude of each shock energy pulse to be delivered to the patient's heart 28 within each tier of therapy, as well as the duration of these shock pulses. Advantageously, such operating parameters may be noninvasively programmed into the memory 44 through a telemetry circuit 46, in telecommunicative contact with an external programmer 48 by way of a suitable coupling coil 50. The coupling coil 50 may serve as an antenna for establishing a radio frequency (rf) communication link 52 with the external programmer 48; or the coil 50 may serve as a means for inductively coupling data to and from the telemetry circuit 46 from and to the external programmer 48. Further, such telemetry circuit 46 advantageously allows status information relating to the operation of the ICD 20, as contained in the control/timing circuit 22 or memory 44, to be sent to the external programmer 48 through the established link 52.

The design, operation and use of the telemetry circuit 46 and external programmer 48 to selectively program operating parameters into the memory 44, or to selectively monitor the operating status of the ICD 20, may be the same as are known in the art. See, e.g., U.S. Pat. No. 4,809,697 (Causey, III et al.) and 4,944,299 (Silvian), incorporated herein by reference.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in the memory 44. The use, design, and operation of microprocessor-based control circuits to perform timing and data analysis functions is known in the art. Alternatively, the control/timing circuit 22 may be realized using conventional logic circuits, e.g., registers, flip-flops, logic gates, and the like, as is also known in the art. The details of the design and operation of the control/timing circuit 22 are not critical to the present invention. Rather, any suitable control/timing circuit 22 may be used that carries out the functions described herein.

In accordance with one embodiment of the present invention, the control/timing circuit 22 determines if an arrhythmia is present by monitoring the four most recent ventricular intervals (e.g., by monitoring the four most recent R-wave-to-R-wave time intervals, hereafter "R-to-R" intervals) following a paced or sensed event in order to anticipate or detect an arrhythmia. The processing circuits within the control/timing circuit 22 then calculate the average rate of the four most recent ventricular intervals and, based on this calculated average rate, make a determination as to whether the average rate indicates a possible arrhythmia. Rate averaging begins when one ventricular interval (R-to-R interval) falls within a programmed arrhythmia rate zone. Following this first ventricular interval within the programmed arrhythmia rate zone, three more consecutive R-to-R intervals must occur to determine the first four-cycle rate average (where "cycle" refers in this context to a cardiac cycle, or the time interval between successive ventricular depolarizations). An ICD device operating in accordance with this embodiment of the invention determines the heart rate based on such a four-cycle average.

It is to be emphasized that although the preferred embodiment monitors the four most recent R-to-R intervals in order to determine the cardiac rate (from which rate a determination is made as to whether an arrhythmia is present), it is apparent that the invention may be practiced by monitoring fewer or greater than four ventricular intervals, or by monitoring atrial intervals (e.g., P-wave-to-P-wave intervals) instead of ventricular intervals.

As previously indicated, the ventricular intervals are monitored by examining the electrical signals that are manifest concurrent with the depolarization or contraction of the cardiac muscle tissue, as sensed through sense amplifier 42. These signals, as they might appear in a typical electrogram (EGM) waveform, are illustrated in FIG. 2. The depolarization and contraction of atrial muscle tissue is manifest by the generation of a P-wave. The depolarization and contraction of ventricular muscle tissue is manifest by the generation of an R-wave (sometimes referred to as the "QRS complex"). The sequence of electrical signals that represent P-waves, followed by R-waves (or QRS complexes) can be sensed from inside of or directly on the heart by using sensing electrodes implanted inside or on the heart, or by using external electrodes attached to the skin of the patient proximate to the heart. The electrical signals representing P-waves and R-waves sensed internal to or directly on the heart are generally referred to as the electrogram (EGM) of the heart; while the electrical signals representing P-waves and R-waves sensed external to the heart, i.e., at the skin of the patient, are usually referred to as the electrocardiogram (ECG) of the heart. A skilled cardiologist or other physician can determine a great deal of information about a patient's heart by simply studying the EGM and/or ECG of the patient. FIG. 2 thus shows an electrogram of the heart and depicts the ventricular interval (R-R interval) as the time interval between successive peaks of the "QRS complex".

The ICD 20 includes means for sensing P-waves and/or R-waves, and hence means for monitoring the patient's EGM. Such means as shown in the functional diagram of FIG. 1 include the sense amplifier 42, the sensing lead 30, and an electrode 32. In order to determine the heart rate, for example, the ICD simply measures the time that elapses between consecutive R-waves. The R-wave is usually used for this determination (as opposed to a P-waves) because the R-wave is normally a much larger signal than the P-wave (because ventricular muscle tissue is much more massive than atrial muscle tissue), and is hence much easier to sense and monitor. However, the same rate determination can also be made by measuring the time between consecutive P-waves, if desired.

Should the monitoring/averaging of the R-to-R interval indicate that an arrhythmia is present, then appropriate circuits included in the control/timing circuit 22 are triggered to apply a prescribed tiered therapy.

The prescribed tiered therapy applied by the ICD 20 may advantageously be programmed into the memory 44. A representative tiered therapy protocol divides therapy into three tiers: ventricular tachycardia low (VT1), ventricular tachycardia high (VT2) and ventricular fibrillation (VF), as shown by the table of FIG. 3. Each tier of therapy corresponds to a rate zone specified by a lower and an upper rate limit of cardiac activity. As seen in FIG. 3, the lowest rate zone, VT1, corresponds to a rate zone defined by cardiac activity that is at least ($\geq$) 150 beats per minute (bpm) and less than (<) 200 bpm. The next higher rate zone, VT2, is defined by cardiac activity that is $\geq$200 bpm and <240 bpm. The highest rate zone, VF, is defined by cardiac activity $\geq$240 bpm. The VT1, VT2 and VF rate zones defined in FIG. 3 are, of course, only exemplary. Other rate zones could be defined as needed and/or desired.

For each of the rate zones shown in FIG. 3 (or for other defined rate zones), a physician may program the energy of the charge (electrical shock) to be delivered to the patient by the output charge generator 26, as well as the number of charges of the specified energy within each rate zone that are to be delivered, in order to most effectively terminate sensed arrhythmias for each particular patient. In addition, the boundaries of each rate zone need not be fixed. A physician may change the rate zone boundaries in accordance with the needs of a particular patient, or the ICD may automatically adjust the rate zone boundaries in accordance with prescribed protocols.

Rate averages greater than or equal to the lowest programmed rate threshold (e.g., $\geq$150 bpm for the zone boundaries defined in FIG. 3) are sorted by rate zone. Sorting occurs using counters included within the control/timing circuit 22 of the ICD 20. A counter exists for each "rate bin", where a rate bin corresponds to a particular rate zone defined by the programmed rate thresholds. Thus, with reference to FIG. 3, there is a VT1 rate bin (and hence a VT1 rate bin counter) for rate zone VT1, a VT2 rate bin (and hence a VT2 counter) for rate zone VT2, and a VF rate bin (and hence a VF counter) for rate zone VF. Such counters may be implemented using hardware, firmware, and/or software included or implemented within the control/logic circuit 22. Each counter accumulates the number of rate averages that occur within its respective rate zone. For each programmed rate zone, a threshold count, referred to as the "Tach Count criteria", defines the number of counts that must accumulate in that rate bin before a determination is made that an arrhythmia has been detected corresponding to that rate zone. Advantageously, the Tach Counts criteria may be independently programmed for each enabled rate zone.

During an arrhythmia classification, another counter included within the control/timing circuits 22, termed a "termination counter", is incremented each time a rate average falls below the lowest programmed zone threshold. Whenever the termination counter counts a specified number of consecutive rate averages below the lowest programmed rate zone threshold, the arrhythmia is classified as terminated. However, if one average rate occurs within a programmed tachycardia rate zone, then the termination counter is reset. Hence, the arrhythmia is classified as terminated only when a specified number of consecutive four-cycle averages fall below the lowest programmed zone threshold. In this manner, neither an arrhythmia event nor the termination of an arrhythmia event is a classification that is easily changed without a consistent underlying cardiac rhythm to support such a change. Hence, short-lived, or brief, one-of-a-kind fast/slow cardiac rhythms or cardiac irregularities are not likely to change the overall arrhythmia classification.

In a preferred embodiment of the ICD 20, before a possible or actual arrhythmia is detected by the ICD, a further requirement, termed the "Sudden Onset Criterion" must be satisfied. The Sudden Onset Criterion prevents the ICD from classifying exercise-induced, gradually-accelerated sinus tachycardia as a ventricular tachycardia. Therefore, patients experiencing normal accelerated heart rates as a result of exercise will not be given ICD therapy by mistake. For the "Sudden Onset Criterion" to be met, there must be an abrupt change in the R-to-R interval, as explained below.

Figure 4B:
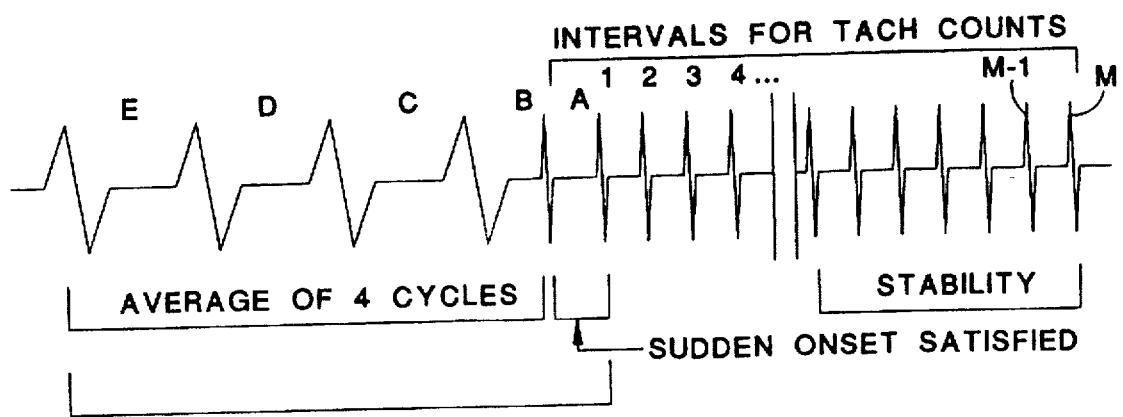

FIGS. 4A and 4B illustrate the definition, detection and application of the Sudden Onset Criterion used within the preferred embodiment of the ICD 20. Shown in FIGS. 4A and 4B are schematic representations of an EGM waveform that represents the rhythm associated with depolarizations and contractions of a patient's heart. As has been previously indicated, a cardiac cycle is preferably measured as the time interval between successive R-waves. Whether the Sudden Onset Criterion has been established is determined by comparing the most recent cardiac interval with the preceding four cardiac intervals. Thus, as seen in FIG. 4A, interval A (the most recent) is compared to the preceding four intervals, B, C, D and E. To satisfy the Sudden Onset criterion both of the following conditions must be met:

1. Interval A (the most recent interval) must be less than a programmable percentage of the average of intervals B, C, D and E, (the four most recent intervals excluding interval A); and 2. Interval A must be less than or equal to the interval defined by the lowest programmed VT rate threshold.

When interval A is less than a prescribed percentage of the average of the preceding four intervals B, C, D and E, that suggests that the most recent cardiac cycle (interval A) is occurring at a much faster cardiac rate than the previous four-cycle average rate, i.e., that there has been a sudden (not a gradual) onset of an arrhythmia. When interval A is less than or equal to the lowest programmed VT interval, that indicates that the faster rate associated with interval A is one that is properly classified as an arrhythmia. (At this point, it may be helpful to emphasize the inverse relationship that exists between heart rate (measured, e.g., in bpm) and the underlying interval (measured in time, e.g., msec) between events that define the heart rate. A long interval corresponds to a slow rate, whereas a short interval corresponds to a fast rate. Thus, for example, an R—R interval of 1000 milliseconds (msec) corresponds to a heart rate of 60 bpm; whereas an R—R interval of 333 msec corresponds to a heart rate of 180 bpm.)

Satisfying the Sudden Onset criterion, by itself, does not establish the presence of an arrhythmia, but it is just one element that must be present. In addition to satisfying the Sudden Onset criterion, the invention also requires that a prescribed number of rate averages must have occurred within the appropriate rate zone —i.e., the Tach Count criteria must be established, as explained above—before a final determination is made that an arrhythmia is present.

Thus, it is seen that a sequence of events, shown in FIG. 4B, must occur in order to detect an arrhythmia event: (1) an average rate based on the four most recent cardiac intervals B, C, D and E, must be determined; (2) the Sudden Onset criterion (if enabled) must be satisfied (which requires a short interval A compared to the average of the previous four intervals B, C, D and E, plus an interval A that is sufficiently short to have it classified as falling within one of the predefined arrhythmia rate zones); and (3) the Tach Count criteria must then be established while the Sudden Onset criterion remains satisfied (i.e. a prescribed number M, i.e., 1, 2, 3 . . . M–1, M, of consecutive short intervals must occur, each of which falls within the predefined arrhythmia rate zone).

The Sudden Onset criterion remains satisfied until:

1. Arrhythmia termination criteria has been satisfied, defined as six consecutive rate averages below the lowest programmed zone threshold), and 2. Eight consecutive non-arrhythmia intervals have elapsed immediately following satisfaction of the arrhythmia termination criterion.

Tiered therapy as described above is implemented by generating, in a controlled time sequence, a series of control signals that activate various elements or features of the ICD 20. Referring again to FIG. 1, for example, when the control/timing circuits 22 determine the need for a moderate or high energy output pulse, an enable signal 60 is sent to the output charge generator 26. The output charge generator 26 includes a charge circuit 54 (which receives the enable signal), an output capacitor(s) 56, a discharge resistor R1 and an output switching network 58. The enable signal 60 enables the charge circuit 54 so that it begins to charge the output capacitor 56 using power derived from a battery 62. As the output capacitor 56 is thus charged, it is monitored via signal line 64 to determine if the charge (voltage) stored thereon is at a prescribed level as determined by the rate zone in which an arrhythmia is detected. The prescribed level is determined from a programmable charge energy parameter(s) stored in the memory 44. Once the prescribed charge level has been reached, which may take several seconds depending upon the charge level desired, the output capacitor 56 thereafter stands ready to discharge the energy stored thereon through the output switch 58 to the heart 28. Thus, another control signal 66 controls the output switch network 58 so as to cause the high energy stimulus stored on the output capacitor 56 to be delivered to the heart at a prescribed time.

As indicated above, the control/timing circuit 22 may be implemented using conventional logic circuitry, e.g., registers, flip flops and logic gates, and/or logic gate arrays. Such may be configured, e.g., to operate as a state machine. The use of state machine logic circuitry to control an implantable medical device is described, e.g., as shown in U.S. Pat. No. 4,712,555 (Thornander et al.), incorporated herein by reference.

Alternatively, and preferably, the control/timing circuit 22 and memory circuitry 44 may be implemented using a suitable microprocessor. In such instance, an operating program is stored in the memory 44 to control the operation of the microprocessor. Typically, such operating program is permanently stored in a read only memory (ROM) included as part of the memory 44 of the microprocessor 68, while certain operating parameters or variables associated with the operating program may be downloaded from the external programmer 48 to random access memory (RAM), also included as part of the memory 44. The use of a microprocessor to control an implanted medical device is described, e.g., in U.S. Pat. No. 4,940,052 (Mann et al.), incorporated herein by reference.

Figure 5A:
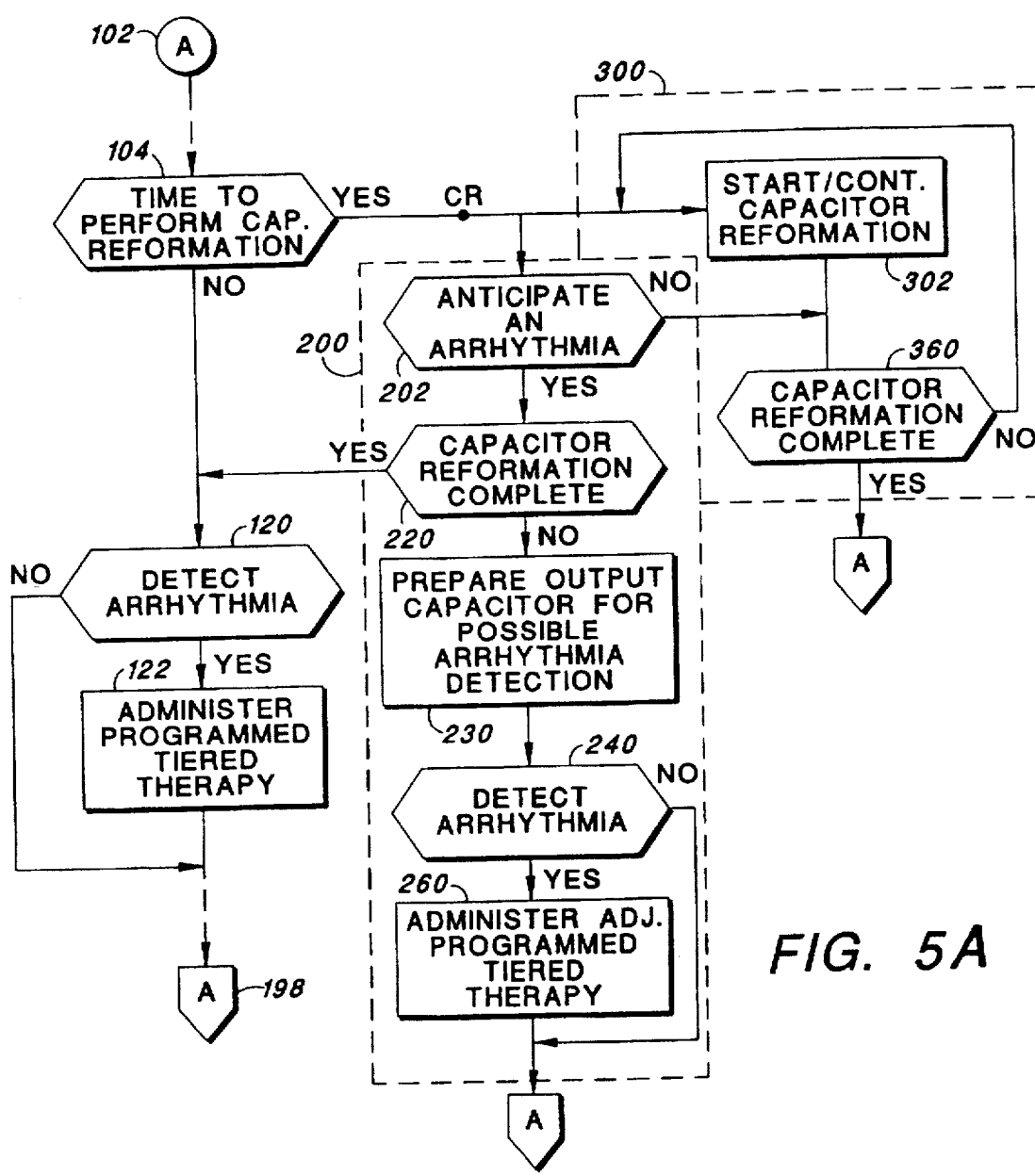
FIG. 5A is a flowchart that provides an overview of the operation of the ICD of FIG. 1 as it carries out the method(s) of the present invention.

Referring next to FIG. 5A, there is shown a flow diagram that provides an overview of the operation of the ICD of FIG. 1 when operating in accordance with the present invention. Such operation not only provides an optimal capacitor reformation, but also controls the delivery of therapy when an arrhythmia is detected during capacitor reformation in a way that minimizes overdosing and causes subsequent shocks of the therapy to be of increasing magnitude. Each main step of the operation shown in FIG. 5A is represented as a block or box, having a corresponding reference numeral. Rectangular-shaped boxes or blocks typically represent a process or event or series of events that occur in order to realize the function indicated, whereas diamond-shaped (or hexagonal-shaped) boxes or blocks usually represent a determination or decision that must be made, which decisions typically have at least two possible outcomes, e.g., YES or NO.

It is noted that the steps shown in FIG. 5A to control an ICD device, as well as those shown in the flowcharts of FIGS. 5B and 5C described below, may be carried out by those of skill in the art using control/logic circuitry 22 based on either a programmed microprocessor, a hardwired state machine logic circuit, or other equivalent circuits, as is known in the art. Indeed, the present invention is not dependent upon or limited by a specific type of circuitry or electronic programmable device used to control the ICD. Rather, it is contemplated that the invention may be carried out using a wide variety of components, circuits, and/or programmable devices.

It is noted that in the operation of a typical ICD device, several different functions and operations may be carried out, many of which are not relevant to the present invention. All such operations may be included in the main flow branch or loop shown on the left side of FIG. 5A that begins with the "A" start block 102, and continues in a straight path to the "A" connector block 198, and is hereafter referred to as the "main control loop A—A".

For purposes of the present invention, at least two determinations must be made at some point in the main control loop A—A. A first determination is whether it is time to perform capacitor reformation (block 104). Typically, capacitor reformation will be performed on a scheduled basis, e.g., once a day (24 hours), once a month (30 days), or once every other month (e.g., 64 days). If it is not time to perform capacitor reformation (NO branch of block 104), then control continues through the main control loop A—A. If it is time to perform capacitor reformation (YES branch of block 104), then two separate branches, outside of the main control loop A—A, are begun. A first branch 200 relates to monitoring the heart rhythm in order to determine whether an arrhythmia is anticipated and, if so, preparing the output capacitor for an arrhythmia should one subsequently be detected. A second branch 300 relates to actually carrying out the capacitor reformation process.

A second determination made in the main control loop A—A of the ICD device shown in FIG. 5A is whether an arrhythmia has been detected (block 120). If an arrhythmia is detected (YES branch of block 120), then an appropriate tiered therapy is administered (block 122), as is known in the art. If an arrhythmia is not detected (NO branch of block 120), then tiered therapy is bypassed.

It is noted that if a determination is made that it is time to perform capacitor reformation (YES branch of block 104), then capacitor reformation (CR) begins (block 302 in the second branch 300), and the steps relating to anticipating an arrhythmia and preparing the output capacitor for a possible arrhythmia detection are carried out (first branch 200). The steps of the first branch 200 and the second branch 300 are carried out essentially independent of each other (although there is by necessity some cross-talk between the two branches, i.e., the first branch needs to know from the second branch whether capacitor reformation has been completed). An overview of the steps carried out in the first branch 200 are included in FIG. 5A. A more detailed representation of these steps is presented in FIG. 5B. A more detailed representation of the capacitor reformation steps carried out in the second branch 300 are presented in FIG. 5C.

Still referring to FIG. 5A, it is seen that an initial step in the first branch 200 (initiated whenever a determination is made in the main control loop A—A that it is time to perform capacitor reformation) is to determine whether an arrhythmia is anticipated (block 202). If an arrhythmia is not anticipated (NO branch of block 202), then reference is made to the capacitor reformation control loop 300 to determine if capacitor reformation is complete (block 360). If not, then monitoring for an anticipated arrhythmia continues (blocks 202, 360) for so long as the capacitor reformation is being carried out.

If a determination is made that an arrhythmia is anticipated (YES branch of block 202), then another determination must be made as to whether capacitor reformation has been completed (block 220). If capacitor reformation is complete (YES branch of block 220), then control returns to the main control loop A—A for a determination as to whether an arrhythmia has been detected (block 120). If capacitor reformation is not complete (NO branch of block 220), then the output capacitor is prepared for a possible arrhythmia detection (block 230). It is these combined steps of anticipating an arrhythmia (block 202) while capacitor reformation is still in process (NO branch of block 220) and, in response, preparing the output capacitor for a possible arrhythmia detection (block 230) that are at the hub of the present invention. If an arrhythmia is detected (YES branch of block 240) after or while the output capacitor has been or is being prepared for such detection, then an appropriate adjusted tiered therapy is provided (block 260). Such adjusted tiered therapy, as explained elsewhere herein, includes shocking the patient with whatever charge is on the output capacitor as soon as the arrhythmia is detected, and then taking steps to ensure that any subsequent shocks needed will be of an increasing value from the first shock (i.e., the tiered therapy is "adjusted", as required, so that the delivered shocks are of increasing magnitude).

Figure 5B:
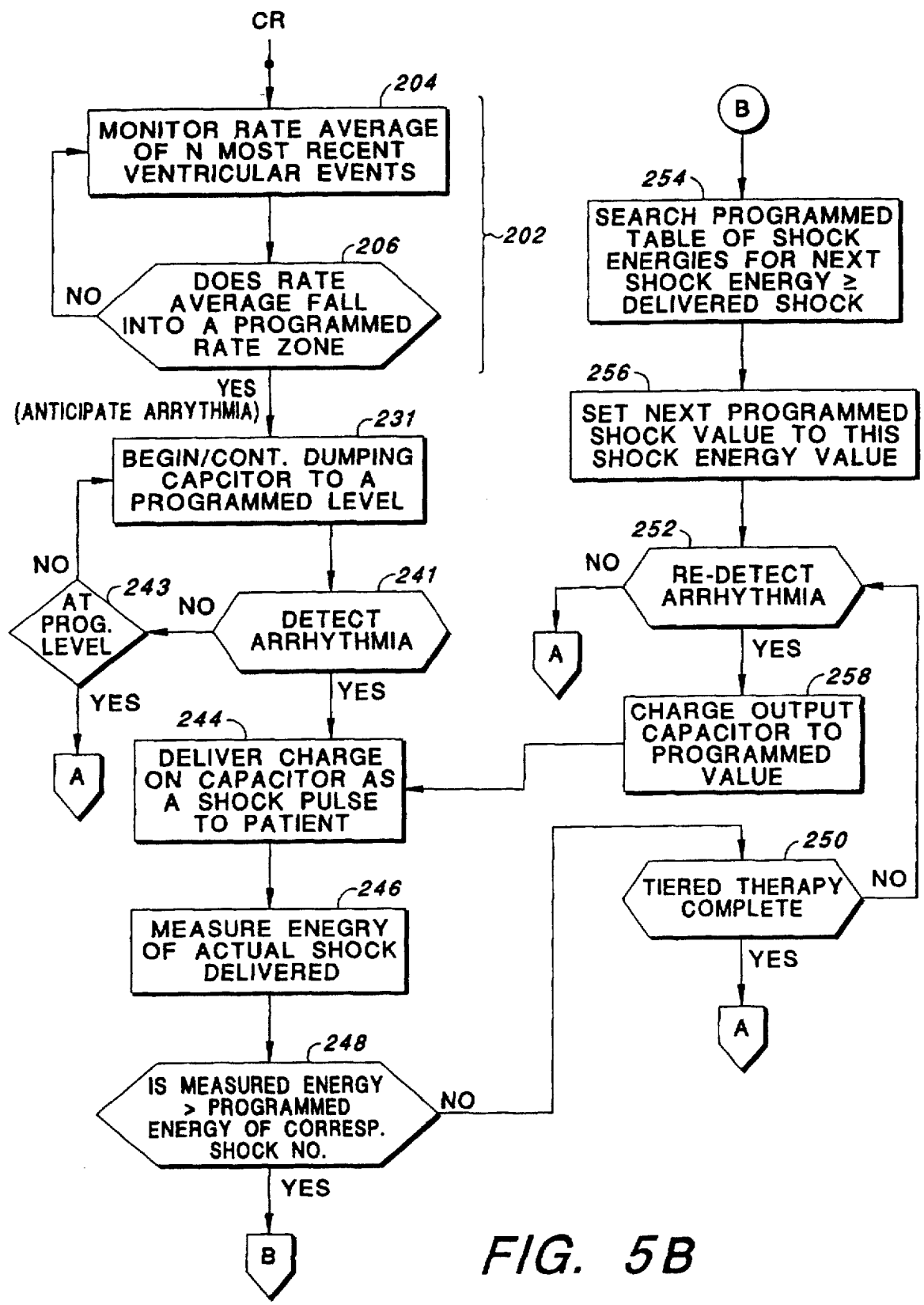
FIG. 5B is a flowchart that provides additional detail for the anticipating-an-arrhythmia branch of FIG. 5A.

Turning next to FIG. 5B, a more detailed flowchart is shown illustrating one manner in which the first branch 200 of FIG. 5A may be carried out. As seen in FIG. 5B, an arrhythmia is anticipated (block 202) by monitoring the rate average of the N most recent ventricular events (block 204), e.g., as explained above in connection with FIG. 4A. If the rate average falls into a programmed rate zone (YES branch of block 206), then an arrhythmia is anticipated.

Once an arrhythmia is anticipated, then the output capacitor is prepared for a possible future arrhythmia detection by beginning to dump the charge on the capacitor to a programmed level (block 231). This charge dumping continues for so long as an arrhythmia is not detected (NO branch of block 241) and the programmed level has not been reached (NO branch of block 243). If the programmed level is reached before an arrhythmia is detected (YES branch of block 243), then control returns to the main control loop A—A (FIG. 5A) for possible subsequent arrhythmia detection (block 120) and subsequent tiered therapy (block 122).

Should an arrhythmia be detected (YES branch of block 241) before the charge on the output capacitor has been dumped to its programmed level, then the charge on the output capacitor is immediately delivered as a shock to the patient (block 244) and the energy of the shock actually delivered is measured (block 246). A determination is then made as to whether the measured shock energy is greater than the programmed energy for the corresponding shock number (block 248), e.g., the first programmed shock. If not (NO branch of block 248), then a determination is made as to whether the tiered therapy is complete (block 250), i.e., whether all of the programmed shocks of the tiered therapy have been delivered. If so (YES branch of block 250), then control returns to the main control loop A—A of the ICD device (FIG. 5A). If not (NO branch of block 250), then a determination is made as to whether an arrhythmia has been redetected (block 252). If so (YES branch of block 252), then the output capacitor is charged to its programmed value (block 258), and the programmed charge is delivered as a shock to the patient (block 244). Again, the energy of the shock may be measured and compared to the programmed energy (block 248, which comparison should yield, in this instance where the capacitor was first charged to the programmed value at block 258, that the measured and programmed values are the same), until the tiered therapy is complete (YES branch of block 250), or until no further redetections of an arrhythmia occur (NO branch of block 252).

If the measured energy of the delivered shock is greater than the programmed energy (YES branch of block 248), which is most likely to occur when the first shock is applied while the output capacitor is still being dumped during capacitor reformation, then a programmed table of shock energies is searched for the next shock energy that is greater than or equal to the delivered shock (block 245). The next programmed shock value is then set to this shock energy value (block 256). Should an arrhythmia then be redetected (YES branch of block 252), the output capacitor is charged to this programmed value (block 258), and the programmed charge is delivered to the patient as a shock pulse (block 244). In this manner, the patient is assured that any subsequent shock pulses associated with the adjusted tiered therapy, if needed, will always be of increasing magnitude from the first pulse that is delivered.

Advantageously, the units of measure of the voltage/ energy in the ICD memory for the programmed parameter voltage may be the same as the units of measure that can be measured directly from the high voltage hardware. (Such units may be, e.g., volts, which is not a pure energy measure, but which is relatable to energy. Alternatively, the units may be joules or millijoules.) Therefore the programmed parameters can be efficiently searched for the next shock energy that is greater than the shock delivered. If the energy of the delivered shock is sufficiently greater than the programmed shock energy, this search for the next programmed shock can cause rezoning of the arrhythmia to a higher rate zone, just as exhaustion of shocks within a lower rate zone can cause rezoning.

Figure 5C:
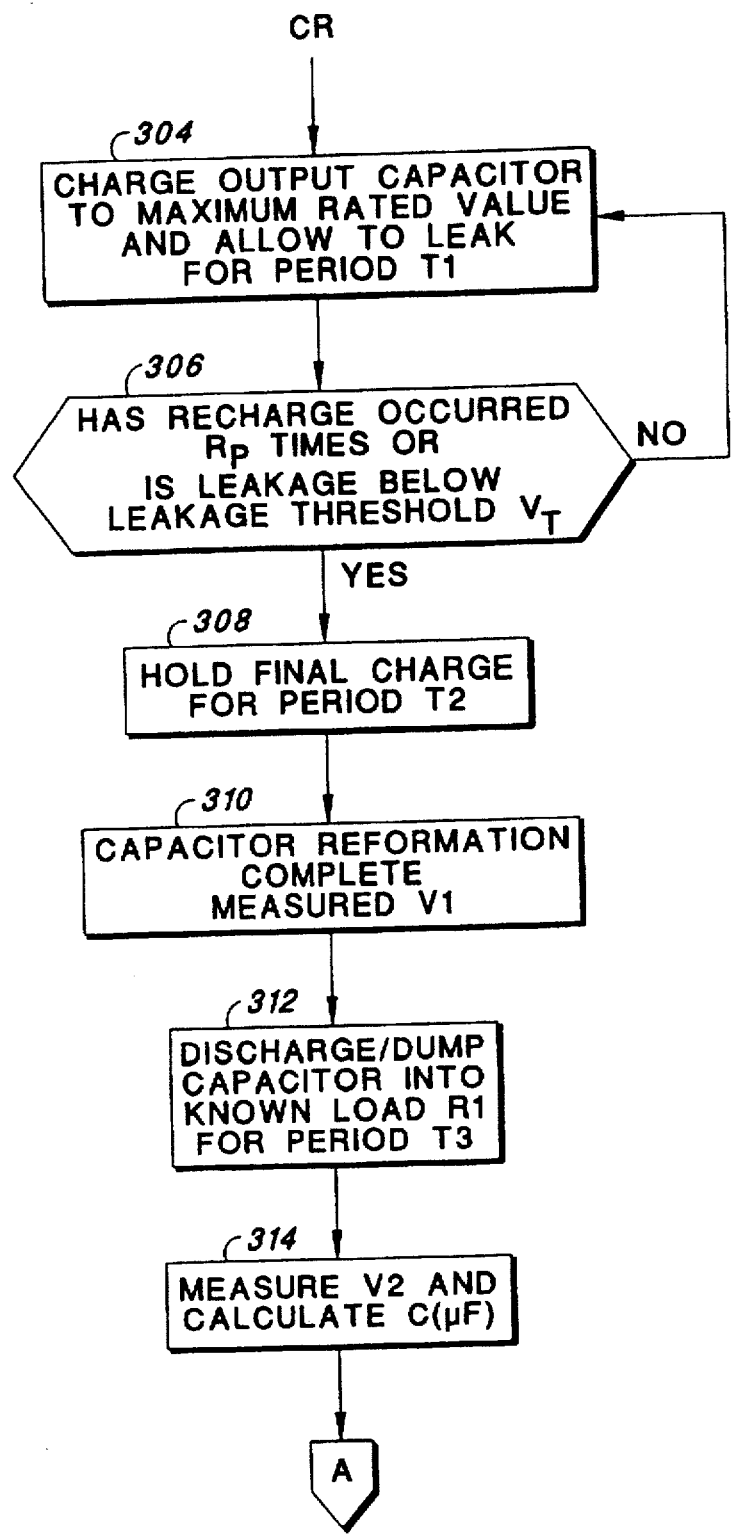
FIG. 5C is a flowchart that provides additional detail for the capacitor reformation block of FIG. 5A.
Figure 6:
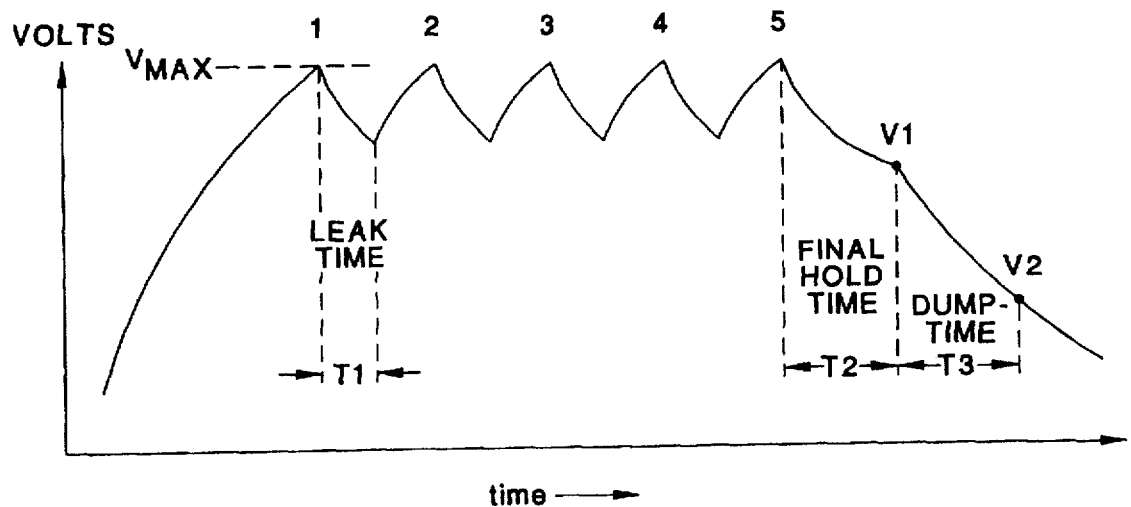
FIG. 6 is a graph that illustrates the voltage (charge) level on the output capacitor of an ICD as a function of time during the capacitor reformation and capacitance measurement processes carried out in accordance with one embodiment of the present invention.
Figure 7:
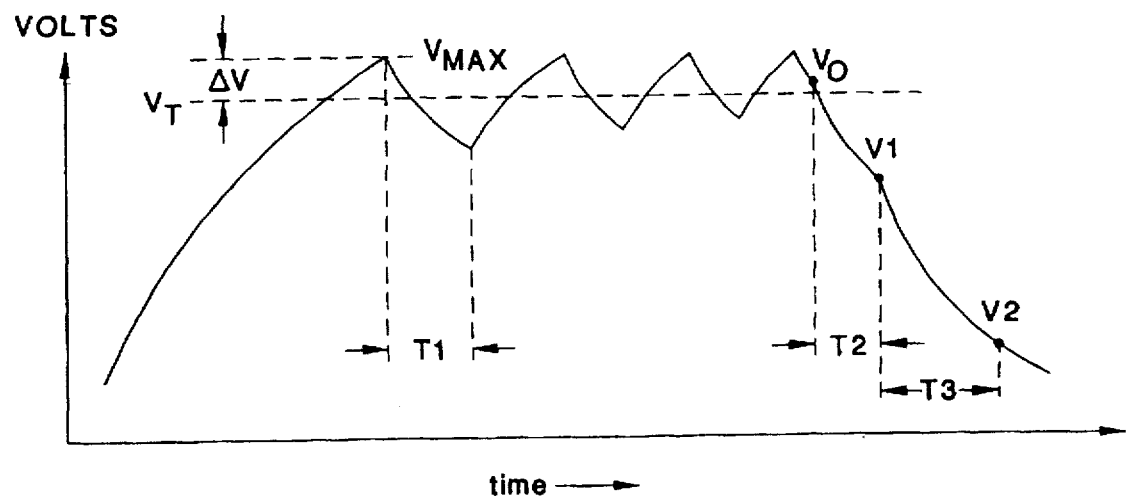
FIG. 7 is a graph that illustrates the voltage (charge) level on the output capacitor as a function of time during the capacitor reformation and capacitance measurement processes carried out in accordance with another embodiment of the present invention.

Referring next to FIGS. 5C, 6 and 7, the steps associated with carrying out capacitor reformation in accordance with the invention are illustrated. Once capacitor reformation (CR) has been started, i.e., once a determination has been made that it is time to perform capacitor reformation (block 104 of FIG. 5A), the output capacitor of the ICD is charged to a maximum energy, e.g., 40 joules, and this maximum energy is then allowed to leak off the capacitor for a time period T1 specified by a leak-time parameter (block 304). Following each charging and leaking of the output capacitor, a determination is made as to whether the output capacitor has been charged and leaked a specified number of times (block 306), where the specified number of times is defined by a recharge parameter ($R_p$). In the event that it is determined that the output capacitor has not undergone the specified number of recharges, the output capacitor is once again charged to a maximum energy level and the charge is allowed to leak off for a time period defined by the leak-time parameter T1. In the event that it is determined that the output capacitor has been charged and leaked the required number of times as specified by the recharge parameter ($R_p$), the final charge is held on the capacitor for a time period specified by a final-hold parameter (T2) (block 308). Upon completion of the time period T2 specified by the final-hold parameter, an initial voltage (V1) on the capacitor is measured (block 310). The charge on the capacitor is then dumped into a known resistance R1, e.g., 50 Kohms, for a time period T3 specified by a dump-time parameter (block 312). The known resistance R1 is connected to the output switch 58 (FIG. 1), or otherwise selectively coupled to the output capacitor during the specified dump-time period. Upon completion of the time period T3 specified by the dump-time parameter, a final voltage (V2) on the output capacitor is measured and the capacitance of the output capacitor is calculated (block 314) using the measured values of the initial voltage V1 and final voltage V2, the known resistance value R1, and the dump-time parameter T3, using the following equation:

$$V2 = V1 \times \exp(-T3/R1 \cdot C).$$

Upon completion of the capacitance calculation, the ICD resumes normal ICD operation, i.e., returns to the main control loop A—A (FIG. 5A), which means, in so far as capacitor reformation is concerned, it waits for the next time capacitor reformation is started (block 104).

FIG. 6 is a timing waveform diagram that illustrates the waveform of the voltage on the output capacitor during the capacitor reformation and capacitance measurement process as described above. As seen in FIG. 6, the leak-time parameter T1 is the time interval following each charging of the output capacitor to a maximum energy level; the recharge parameter $R_p$, specifies the number of times the output capacitor is charged and leaked ($R_p$ is 5 for the waveform shown in FIG. 6, i.e., the capacitor is charged to its maximum voltage five times); the final-hold parameter T2 specifies the length of time a final charge is held (i.e. allowed to decay) on the output capacitor; V1 is the voltage on the capacitor at the end of the hold time period specified by the final-hold parameter T2; the dump-time parameter T3 is the specified period of time in which the charge on the output capacitor C is dumped into a known resistance R1; and V2 designates the voltage level on the output capacitor C immediately following the time period specified by the dump-time parameter T3.

In another embodiment or variation of the invention, illustrated by the voltage waveform shown in FIG. 7 (and also covered by the steps shown in FIG. 5C), the output capacitor C may be charged to its maximum energy level $V_{MAX}$ and allowed to leak for a time period specified by the leak-time parameter T1 (block 304)). The voltage on the capacitor C after the time period T1 is then compared against a leakage threshold $V_T$ (block 306). That is, after a time period T1, the amount of voltage or charge that has leaked off of the capacitor should be no more than an amount $\Delta V$, leaving a voltage on the capacitor of at least $V_{MAX} - \Delta V = V_T$. If capacitor reformation is needed, the amount of charge that leaks from the capacitor during the time period T1 will likely be greater than $\Delta V$, meaning that the voltage remaining on the capacitor after the time period T1 will be less than $V_T$. If so, i.e., if the voltage on the capacitor after the discharge time period T1 is less than $V_T$, then the capacitor is again charged to $V_{MAX}$ and allowed to discharge for a time T1. This process continues—charging and leaking/discharging (blocks 304, 306)—until the voltage remaining on the output capacitor C at the conclusion of a leak/discharge period T1 is greater than or equal to $V_T$, ensuring that the reformation process has continued for an adequate number of "reforming" cycles. For the example shown in FIG. 7, it is seen that four "reforming" cycles occur before the output voltage $V_O$ is greater than $V_T$ after the leak/discharge time T1. Once the output voltage is above the leakage threshold $V_T$, then the final charge on the output capacitor is held, i.e., allowed to leak, for a final duration T2 specified by the final-hold parameter (block 308). The process then continues following the steps described above as shown in FIG. 5-3 (blocks 310 through 314).

Referring to the main control loop A—A shown in FIG. 5A, it is noted that appropriate criteria are used to detect an actual arrhythmia (block 120). For example, the average rate of the four most recent ventricular intervals is monitored. If the rate averages immediately following the first rate average which fell into an arrhythmia rate zone also fall within an arrhythmia rate zone, the ICD sorts and counts the rate averages in a rate-bin corresponding to the rate zone. When the count within a given rate-bin reaches the prescribed threshold (e.g., when the prescribed number of Tach Counts have occurred), an arrhythmia is deemed to exist in the rate zone corresponding to the rate bin.

Using rate averages as described above, or using the other criteria herein described, to determine the onset of an arrhythmia is far superior to simply using the heart rate as the sole criterion. If only the heart rate were used, a patient with regular premature ventricular contractions (PVC's) might be deemed to have an arrhythmia and the output capacitor of his or her ICD would never be reformed. For example, a patient suffering from a bigeminal heart condition has alternating slow and fast heart beats at his or her normal heart rate. If an ICD simply detected the rate of each interval in order to anticipate or detect arrhythmias, each time a fast heart beat was detected the ICD would erroneously anticipate a possible arrhythmia detection and postpone capacitor reformation or dump the output capacitor before the capacitor reformation process could be completed. Therefore, by using rate averages as herein described, the ICD takes into account the heart rhythms of patients suffering from the bigeminal condition, and similar heart conditions, while still providing for capacitor reformation and the delivery of therapy when needed.

ICD capacitor reformation, in accordance with the present invention, is performed automatically and the reformation interval is programmable. If no reformation interval is specified, a default interval is used. The default interval may be any suitable value, e.g., 64 days.

If before capacitor reformation has been initiated, the ICD anticipates a possible arrhythmia detection, or if an actual arrhythmia is detected, capacitor reformation is not initiated. Rather, capacitor reformation is postponed by a specified amount, e.g., 24 hours±10 minutes.

If dumping occurs during the initial charge cycle of capacitor reformation, e.g., because of an anticipated arrhythmia, then capacitor reformation is similarly postponed by 24 hours±10 minutes. However, if dumping occurs after the initial charge and leak cycle, capacitor reformation is considered complete, which means that capacitor reformation will not commence again until the next programmed time for reformation to begin (e.g., 64 days later).

In a preferred embodiment, if an arrhythmia is detected at any time and a maximum energy cardioversion-defibrillation shock therapy has been delivered to the patient, such shock therapy postpones capacitor reformation by one reformation interval (e.g., 64 days) from the time of the maximum energy shock.

Using the reformation procedure outlined herein eliminates the problems mentioned in the background section of the application. As a safeguard, the ICD may further include a built-in provision whereby, when in the VF rate zone, all shocks from the highest rate zone are always delivered, even if the first shock does not correspond to the first programmed shock energy for the high-rate zone. This safeguard assures that sufficient numbers of shocks are delivered to terminate the arrhythmia, but also assures that there will be no instances of a lesser energy shock being delivered after a larger shock during an arrhythmia episode.

As described above, it is thus seen that the present invention provides an ICD that provides optimal capacitor reformation by allowing successive charging and leaking of an output capacitor for a specified number of times while minimizing delays of therapy to the patient in the event of an arrhythmia detection during capacitor reformation. In addition, the ICD minimizes the risk of overdosing the patient with charge energy and adjusts subsequent therapy to appropriate energy levels in the event that prior therapy has not successfully terminated the arrhythmia.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardioverter/defibrillator (ICD) comprising:

an output capacitor;

means for reforming the output capacitor;

means for anticipating an arrhythmia detection during capacitor reformation;

means for dumping any charge placed on the output capacitor during capacitor reformation to a programmed energy level if an arrhythmia detection is anticipated;

means for detecting an arrhythmia;

means for ceasing any further dumping of the output capacitor if the arrhythmia is detected during capacitor reformation before reaching the programmed energy level; and means for delivering a charge on the output capacitor to a patient if an arrhythmia is detected.

2. The ICD of claim 1, wherein said means for anticipating an arrhythmia detection comprises:

means for monitoring an average rate of the N most recent ventricular intervals, where N is an integer greater than one; and means for determining if the average rate of the N most recent ventricular intervals falls within a programmed rate zone, and if so, anticipating an arrhythmia corresponding to that rate zone.

3. The ICD of claim 2, wherein said means for monitoring the rate average of the N most recent ventricular intervals comprises a rate bin for each of a plurality of rate zones, and means for incrementing each rate bin whenever an average rate is detected that falls within the rate zone corresponding to the rate bin.

4. The ICD of claim 3, wherein said means for detecting an arrhythmia comprises means for determining if a given rate bin has been incremented M times, where M is an integer greater than one, and wherein an arrhythmia is detected if the given rate bin has been incremented at least M times.

5. The ICD of claim 1, wherein said means for reforming the output capacitor comprises:

means for charging the output capacitor to its maximum charge level and allowing the charge to leak off for a time period specified by a leak-time parameter (T1); and means for recharging the output capacitor a specified number of times, the number of recharges being specified by a recharge parameter ($R_P$).

6. The ICD of claim 5, wherein said means for reforming an output capacitor further comprises:

means for holding a final charge for a time period specified by a final-hold parameter (T2);

means for measuring an initial voltage (V1) on said output capacitor upon completion of the time period specified by the final-hold parameter;

means for dumping the output capacitor into a known resistance value (R1) for a time period specified by a dump-time parameter (T3);

means for measuring a final voltage (V2) on the output capacitor upon completion of the time period specified by the dump-time parameter; and means for calculating the capacitance of the output capacitor using the measured values of the initial and final voltages, the known resistance value, and the value of the dump-time parameter.

7. The ICD of claim 1, wherein said means for reforming an output capacitor comprises:

means for charging the output capacitor to its maximum charge level and allowing the charge to leak off for a time period specified by a leak-time parameter (T1);

means for measuring a voltage on the output capacitor following each time period specified by the leak-time parameter;

means for comparing the measured voltage to a specified threshold value ($V_T$); and means for continuing to recharge the output capacitor to its maximum charge level and allowing the charge to leak off for the time period specified by the lead-time parameter (T1) until the measured voltage is not below the specified leakage threshold value.

8. The ICD of claim 7, further comprising:

means for holding a final charge for a time period specified by a final-hold parameter (T2);

means for measuring an initial voltage (V1) on the output capacitor upon completion of the time period specified by the final-hold parameter;

means for dumping the charge on the output capacitor into a known resistance value (R1) for a time period specified by a dump-time parameter (T3);

means for measuring a final voltage (V2) on the output capacitor upon completion of the time period specified by the dump-time parameter; and means for calculating the capacitance of the output capacitor using the measured values of the initial and final voltages, the known resistance value, and the value of the dump-time parameter.

9. The ICD of claim 1, further comprising:

memory means for storing a plurality of programmed parameter values of charge energies;

means for measuring a charge energy delivered from the output capacitor following each delivery of charge to a patient;

means for comparing the measured charge energy to a first programmed parameter value, wherein if the measured charge energy level is greater than the first programmed parameter value, a search of the memory means is employed for a second programmed parameter value that is greater than the measured charge energy delivered; and means for setting a value of a next charge energy to be delivered equal to the second programmed parameter value.

10. An implantable cardioverter defibrillator (ICD) comprising:

sensing circuit means for detecting cardiac rhythm through one or more implantable electrodes adapted to be coupled to a patient's heart;

an output capacitor coupled to at least one electrode adapted to be placed on or near the patient's heart through an output switch;

charging circuit means for charging the output capacitor to a programmed charge level;

control circuit means for generating control signals, wherein the control signals are coupled to: (a) the charging circuit means for controlling the charging of the output capacitor during capacitor reformation and during the delivery of a prescribed therapy, (b) the output switch for controlling the closure of the output switch in accordance with the prescribed therapy, and (c) the sensing circuit means for monitoring the average rate of the N most recent cardiac intervals, where N is an integer greater than one;

a rate bin, coupled to the control circuit means, for sorting and storing the number of occurrences of an average rate of the N most recent cardiac intervals falling within a specified arrhythmia rate zone, wherein if a prescribed number of occurrences are stored within a given rate bin, an arrhythmia detection corresponding to the rate zone of the given rate bin is anticipated;

a resistor, coupled to the output capacitor;

means, responsive to anticipating an arrhythmia detection, for dumping the output capacitor through the resistor to a programmed charge level;

means for detecting an arrhythmia; and means for ceasing the dumping of the output capacitor in the event an arrhythmia is detected and the charge on the output capacitor has not yet reached its programmed charge level.

11. The ICD of claim 10, wherein said means for detecting an arrhythmia comprises means for determining if M occurrences are stored within a given rate bin, where M is an integer greater than one, and if so, specifying that an arrhythmia corresponding to the rate zone has been detected.

12. The ICD of claim 11, further comprising:

means for measuring a charge energy delivered from the output capacitor following each delivery of charge to a patient;

memory means for storing a plurality of programmed parameter values of charge energies;

means for comparing the measured charge energy to a first programmed parameter value, wherein if the measured charge energy is greater than the first programmed parameter value, a search of the memory means for a second programmed parameter value that is greater than the measured charge energy; and means for setting a value of a next charge energy to be delivered to the patient to a value equal to the second programmed parameter value.

13. The ICD of claim 10, further comprising:

means for initially charging the output capacitor to a maximum charge level and then allowing the charge to leak off for a time period specified by a leak-time parameter; and means for recharging the output capacitor to its maximum charge level and allowing the charge to leak off for a specified number of times, the number of recharges being specified by a recharge parameter.

14. The ICD of claim 13, further comprising:

means for holding a final charge on the output capacitor for a time period specified by a final-hold parameter;

means for measuring an initial voltage on said output capacitor upon completion of the time period specified by the final-hold parameter;

means for dumping the output capacitor into a known resistance value for a time period specified by a dump-time parameter;

means for measuring a final voltage on the output capacitor upon completion of the time period specified by the dump-time parameter; and means for calculating the capacitance of the output capacitor using the measured values of the initial and final voltages, the known resistance value, and the value of the dump-time parameter.

15. The ICD of claim 10, further comprising:

means for charging the output capacitor to a maximum charge level and then leaking the charge off of the output capacitor for a time period specified by a leak-time parameter;

means for measuring a voltage on the output capacitor following each time period specified by the leak-time parameter;

means for comparing the measured voltage to a specified leakage threshold value; and means for repeating the charging, leaking, voltage measuring, and comparing until the measured voltage is not below the specified leakage threshold value, whereupon the output capacitor is reformed.

16. The ICD of claim 15, further comprising:

means for holding a final charge on the output capacitor, immediately after the output capacitor has been reformed, for a time period specified by a final-hold parameter;

means for measuring a first voltage (V1) on the output capacitor upon completion of the time period specified by the final-hold parameter;

means for dumping the output capacitor into a known resistance value for a time period specified by a dump-time parameter;

means for measuring a second voltage on the output capacitor upon completion of the time period specified by the dump-time parameter; and means for calculating the capacitance of the output capacitor using the measured values of the first and second voltages, the known resistance value, and the value of the dump-time parameter, whereby the capacitance of the output capacitor may be measured each time the output capacitor is reformed.

17. A method of reforming an output capacitor of an implantable cardioverter-defibrillator (ICD), said ICD having means for anticipating an arrhythmia event and means for detecting an arrhythmia event through one or more implantable electrodes coupled to a patient's heart, an output capacitor coupled to the one or more defibrillation electrodes through an output switch, a charging circuit that charges the output capacitor to a programmed energy level, memory means for storing programmed parameters, and a control circuit that generates control signals that are operatively coupled to the charging circuit, memory means, and the output switch for controlling the charging of the output capacitor and the closure of the output switch in accordance with a prescribed therapy, said method comprising the steps of:

(a) reforming the output capacitor at prescribed intervals by charging the output capacitor to a maximum charge value and allowing the charge to leak off for a specified period of time (T1);

(b) checking for an anticipated arrhythmia detection while reforming the output capacitor as set forth in step (a);

(c) ceasing the capacitor reformation of step (a) and dumping the output capacitor to a programmed charge level in the event an anticipated arrhythmia detection occurs in step (b);

(d) checking for an arrhythmia detection while performing the dumping of step (c) and, in the event an arrhythmia detection occurs and the output capacitor has not yet been dumped to its programmed charge level, ceasing the dumping of the output capacitor; and (e) delivering whatever charge is on the output capacitor at the time an arrhythmia detection occurs.

18. The method of claim 17, wherein step (a) of reforming the output capacitor further comprises repeating the charging and leaking of the output capacitor for a prescribed number of recharges.

19. The method of claim 18, wherein the step of reforming the output capacitor further comprises the steps of:

holding a final charge on the output capacitor for a time period specified by a final-hold parameter (T2) after the prescribed number of recharges has occurred;

measuring an initial voltage (V1) on the output capacitor upon completion of the time specified by the final-hold parameter;

dumping the output capacitor into a known resistance (R1) for a time period specified by a dump-time parameter (T3);

measuring a final voltage (V2) on the output capacitor upon completion of the time period specified by the dump-time parameter; and calculating the capacitance of the output capacitor using the measured values of the initial and final voltages, the known resistance, and the value of the dump-time parameter.

20. The method of claim 18, wherein the step of reforming the output capacitor further comprises the steps of:

measuring a voltage on the output capacitor following each recharge and leakage time period specified by a leak-time parameter (T1);

comparing the measured voltage against a specified leakage threshold value ($V_T$); and continuing to recharge the output capacitor and allowing it to leak for the period specified by the leak-time parameter until the measured voltage on the output capacitor is greater than the specified leakage threshold value.

21. The method of claim 20, further comprising the steps of:

holding a final charge on the output capacitor for a time period specified by a final-hold parameter;

measuring an initial voltage on the output capacitor upon completion of the time period specified by the final-hold parameter;

dumping the output capacitor into a known resistance value for a time period specified by a dump-time parameter;

measuring a final voltage on the output capacitor upon completion of the time period specified by the dump-time parameter; and calculating the capacitance of the output capacitor using the measured values of the initial and final voltages, the known resistance value, and the dump-time parameter.

22. The method of claim 17, wherein step (b) of checking for an anticipated arrhythmia detection comprises the steps of:

monitoring a rate average of the N most recent cardiac intervals, where N is an integer greater than one; and checking to see if the rate average falls within a programmed arrhythmia rate zone, and if so, concluding than an arrhythmia detection corresponding to the programmed rate zone is anticipated.

23. The method of claim 22, wherein the step of monitoring an average rate of the N most recent cardiac intervals further comprises sorting and storing the monitored rate averages into respective rate bins, each rate bin corresponding to an arrhythmia rate zone, and wherein the storage of a rate average in a respective rate bin indicates that an arrhythmia detection corresponding to the rate zone is anticipated.

24. The method of claim 23, wherein step (d) of detecting an arrhythmia comprises requiring that at least M occurrences of a rate average of the N most recent cardiac intervals occur in a respective rate bin before indicating that an arrhythmia is detected.

25. The method of claim 17, further comprising the steps of:

(f) measuring the charge delivered from said output capacitor following each delivery of charge to a patient;

(g) comparing the measured charge delivered to a first programmed parameter value, and, in the event the measured charge delivered is greater than the first programmed parameter value, searching a memory table of preprogrammed parameter values for a second programmed parameter value that is greater than the measured charge delivered; and (h) setting a value for a next charge to be delivered to the patient to be equal to the second programmed parameter value.

26. An implantable cardioverter defibrillator (ICD) comprising:

means for selectively delivering electrical shock pulses to a patient;

an output capacitor;

means for charging the output capacitor to a maximum charge level and allowing the charge to leak off for a time period specified by a pre-programmed leak-time parameter (T1);

means for recharging the output capacitor a specified number of times, the number of recharges being specified by a pre-programmed recharge parameter ($R_P$);

means for holding a final charge on the output capacitor, after the capacitor has been recharged $R_P$, times, for a time period specified by a final-hold parameter (T2); and means for calculating the capacitance of the output capacitor.

27. The ICD of claim 26, wherein the means for calculating the capacitance of the output capacitor comprises:

means for measuring an initial voltage (V1) on the output capacitor upon completion of the time period specified by the final-hold parameter;

means for dumping the charge on the output capacitor into a known resistance value (R1) for a time period specified by a dump-time parameter (T3);

means for measuring a final voltage (V2) on the output capacitor upon completion of the time period specified by the dump-time parameter; and means for calculating the capacitance of the output capacitor using the measured values of V1 and V2.

28. An implantable cardioverter defibrillator (ICD) comprising:

means for selectively delivering electrical shock pulses to a patient;

an output capacitor;

means for charging the output capacitor to a maximum charge level and allowing the charge to leak off for a time period T1;

means for measuring a voltage on the output capacitor following each time period T1;

means for comparing the measured voltage to a specified leakage threshold value, $V_T$; and means for continuing to recharge the output capacitor to its maximum charge level and allowing the charge to leak off for the time period T1 until the measured voltage at the end of the time period T1 exceeds the specified leakage threshold value, $V_T$.

29. The ICD of claim 28, further comprising:

means for holding a final charge on the output capacitor for a time period T2;

means for measuring an initial voltage V1 on the output capacitor upon completion of the time period T2;

means for dumping the charge on the output capacitor into a known resistance value R1 for a time period T3;

means for measuring a final voltage V2 on the output capacitor upon completion of the time period T3; and means for calculating the capacitance of the output capacitor using the measured values of V1 and V2 the known resistance value R1, and the dump-time T3.

30. A method of capacitor reformation in an implantable cardioverter defibrillator (ICD) device, the method comprising the steps of:

(a) charging an output capacitor of the ICD to a maximum charge level ($V_{MAX}$) and allowing the charge to leak off of the output capacitor for a time period specified by a leak-time parameter (T1); and (b) recharging the output capacitor with a series of recharges, the total number of recharges being specified by a recharge parameter ($R_P$);

(c) holding a final charge (V1) on the output capacitor for a time period specified by a final-hold parameter (T2); and (d) calculating the capacitance of the output capacitor.

31. The method of claim 30, wherein the step of calculating the capacitance of the output capacitor comprises the steps of:

(a) measuring an initial voltage (V1) on the output capacitor upon completion of the time period specified by the final-hold parameter (T2);

(b) dumping the charge on the output capacitor into a known resistance value (R1) for a time period specified by a dump-time parameter (T3);

(c) measuring a final voltage (V2) on the output capacitor upon completion of the time period (T3) specified by the dump-time parameter; and (d) calculating the capacitance of the output capacitor using the measured values of the initial and final voltages, the known resistance value, and the dump-time parameter.

32. A method of capacitor reformation in an implantable cardioverter defibrillator (ICD) device, the method comprising the steps of:

(a) charging an output capacitor of the ICD to a maximum charge level ($V_{MAX}$) and allowing the charge to leak off of the output capacitor for a time period specified by a leak-time parameter (T1);

(b) measuring the charge on an output capacitor following the time period specified by the leak-time parameter;

(c) comparing the measured charge against a specified leakage threshold value ($V_T$); and (d) continuing to recharge the output capacitor to $V_{MAX}$ and allowing the charge to leak off for the time period T1 until the measured voltage after the time period T1 exceeds the specified leakage threshold.

33. The method of claim 32, further comprising the steps of:

(e) holding a final charge on the output capacitor after step (d) for a time period specified by a final-hold parameter (T2);

(f) measuring an initial voltage (V1) on the output capacitor upon completion of the time period specified by the final-hold parameter;

(g) dumping the charge on the output capacitor into a known resistance value (R1) for a time period specified by a dump-time parameter (T3);

(h) measuring a final voltage (V2) on the output capacitor upon completion of the time period specified by the dump-time parameter; and (i) calculating the capacitance of the output capacitor using the measured values of the initial and final voltages, the known resistance value, and the dump-time parameter.

34. A method of dynamically adjusting charge energy values of an implantable cardioverter defibrillator (ICD) device to appropriate programmed energy levels following every charge delivery to a patient, said ICD device employing tiered level therapy and having memory means for storing programmed parameters corresponding to charge energy values for each level of therapy, said method comprising the steps of:

(a) measuring a charge energy delivered to a patient following each charge delivery;

(b) comparing the measured charge energy to a first programmed parameter corresponding to a charge energy value for a desired tier of therapy;

(c) searching the memory means, in the event that the measured charge energy is found to be greater than the first programmed parameter in step (b), for a second programmed parameter that is greater than the measured charge energy; and (d) setting the value of the next programmed charge energy to be delivered to a patient to the second programmed parameter value.

* * * * *